United States Patent
Duplat et al.

(10) Patent No.: US 12,178,538 B2
(45) Date of Patent: Dec. 31, 2024

(54) ROTARY MICROMOTOR

(71) Applicant: ROBEAUTE, Paris (FR)

(72) Inventors: Bertrand Duplat, Paris (FR); Ali Oulmas, Paris (FR); Philippe Planard, Paris (FR)

(73) Assignee: ROBEAUTE, Paris (FR)

( * ) Notice: Subject to any disclaimer, the term of this patent is extended or adjusted under 35 U.S.C. 154(b) by 214 days.

(21) Appl. No.: 18/004,771

(22) PCT Filed: Jul. 9, 2021

(86) PCT No.: PCT/EP2021/069196
§ 371 (c)(1),
(2) Date: Jan. 9, 2023

(87) PCT Pub. No.: WO2022/008729
PCT Pub. Date: Jan. 13, 2022

(65) Prior Publication Data
US 2023/0255710 A1    Aug. 17, 2023

(30) Foreign Application Priority Data
Jul. 10, 2020 (EP) .................................... 20305797

(51) Int. Cl.
  *F16H 25/12* (2006.01)
  *A61B 34/00* (2016.01)
  *A61B 17/00* (2006.01)

(52) U.S. Cl.
  CPC ............. *A61B 34/72* (2016.02); *F16H 25/12* (2013.01); *A61B 2017/00345* (2013.01); *F16H 2025/127* (2013.01)

(58) Field of Classification Search
  CPC ... F16H 2025/127; F16H 25/12; A61B 34/72; A61B 2017/00345
  See application file for complete search history.

(56) References Cited

PUBLICATIONS

Prisacariu et al. "A general view on the classification and operating principle of piezoelectric ultrasonic motors" (Year: 2012).*
Liu et al. "A Review of Locomotion Systems for Capsule Endoscopy" (Year: 2015).*
Fu et al. "Characteristic Evaluation of a Shrouded Propeller Mechanism for a Magnetic Actuated Microrobot" (Year: 2015).*
Huda et al. "Robots for minimally invasive diagnosis and intervention" (Year: 2016).*

(Continued)

*Primary Examiner* — Randell J Krug
(74) *Attorney, Agent, or Firm* — Maier & Maier, PLLC

(57) ABSTRACT

A micro-engine including a rotation structure, the rotation structure including a head portion, a rear portion, and a deformable portion connecting both portions. The deformable portion is deformable in elongation or compression along a main axis and includes a spring element displaying a free end. The free end of the spring element includes at least an abutment member. The deformable portion further includes a wheel-platform which displays a first and a second face, being configured to cooperate with the free end of the spring element in order to transform a back-and-forth movement of the at least one spring element into a rotational movement of the wheel-platform.

15 Claims, 8 Drawing Sheets

(56) References Cited

PUBLICATIONS

Pham et al. "Micro cam system driven by electrostatic com-drive actuators based on SOI-MEMS technology" (Year: 2014).*
International Search Report issued on Oct. 20, 2021 in corresponding International application No. PCT/EP2021/069196; 3 pages.
Prisacariu et al., "A general view on the classification and operating principle of piezoelectric ultrasonic motors", Electrical and Power Engineering (EPE), 2012 International Conference and Exposition on, IEEE, Oct. 25, 2012, pp. 409-414, XP032425256.
Liu et al: "A Review of Locomotion Systems for Capsule Endoscopy", IEEE Reviews in Biomedical Engineering, vol. 8, Aug. 17, 2015 (Aug. 17, 2015), pp. 138-151, XP011666734.
Fu et al: "Characteristic Evaluation of a Shrouded Propeller Mechanism for a Magnetic Actuated Microrobot", Micromachines, vol. 6, No. 9, Sep. 3, 2015 (Sep. 3, 2015), pp. 1272-1288, XP055762567.
Huda et al: "Robots for minimally invasive diagnosis and intervention", Robotics and Computer Integrated Manufacturing, Elsevier Science Publishers, vol. 41, Apr. 6, 2016 (Apr. 6, 2016), pp. 127-144, XP029541151.
Pham et al: "Micro cam system driven by electrostatic comb-drive actuators based on SOI-MEMS technology", Microsystem Technologies, Berlin, De, vol. 21, No. 3, Jan. 29, 2014 (Jan. 29, 2014), pp. 699-706, XP035447889.

* cited by examiner

ROTARY MICROMOTOR

FIELD OF INVENTION

The present invention relates to a rotary micromotor allowing a micro-structure or micro device to move through a viscous material, in particular through an organ of a subject such as a brain.

BACKGROUND OF INVENTION

The ability to reach deep and functional structures without damage is a major challenge in mini-invasive surgery, especially in neurosurgery. Thanks to micro-technologies, it becomes possible to send micro-structures or micro devices inside an organ of a subject, such as a brain. However, the propulsion of a micro-structure in an environment at low Reynolds number as is the brain, is a challenge due to the absence of inertia and the presence of relatively high drag forces induced by the small size of the micro-structure.

The most effective way for a micro-structure or micro-device to move through a viscous material, as for example the brain, is to rotate while moving forward. Said micro-structure therefore needs a rotary micro-motor (or micro-engine) to allow this most effective moving way.

Today, rotary micro-engines are typically using three coils positioned in a circular fashion. Those three coils take too much space and therefore limit possibilities to reach sub-millimetric diameter necessary in micro-engineering.

Application CN108964514 is known, it discloses a rotating micro-motor driven by a piezoelectric and shape memory alloy and a driving method thereof. The rotating micro-motor comprises an upper cover, a housing, an elastic seat, a base, bearing end covers, a rotor, a compression spring, a support frame, a rotating shaft, a deep groove ball bearing, an adapter, a piezoelectric stack, an adjusting screw, a shape memory alloy wire, a friction block, a rubber friction pad, a one-way rolling bearing, an elastic stop ring, a displacement amplifying rod and a rotating body which are successively stacked from top to bottom. The bearing end covers are installed on the central positions of the upper surface of the upper cover and the lower surface of the base. The driving method changes the deformation of the piezoelectric stack by a triangular wave signal, thereby rotating the rotating body by the displacement amplifying rod so as to rotate the support frame. Further, the deformation of the shape memory alloy wire is changed by a half triangular wave signal, and the friction block is pushed by the spring to come into contact with the rotor, thereby realizing the rotating operation of the rotor. This invention does not allow moving through a viscous material.

In this context, the invention is intended to propose a rotary micro-engine allowing a micro-structure to move forward in a highly efficient way through a fluidic environment at low Reynolds number.

SUMMARY

This invention thus relates to a micro-engine configured to move a micro-structure, the micro-engine comprising a rotation structure, said rotation structure comprising a head portion, a rear portion and a deformable portion connecting the head portion and the rear portion,
wherein the deformable portion is deformable in elongation or compression along a main axis extending from the head portion to the rear portion,
wherein the deformable portion comprises at least one spring element, the at least one spring element having a rear end attached to the rear portion, the at least one spring element displaying a free end,
wherein the free end of the at least one spring element comprises at least an abutment member,
wherein the rotation structure further comprises an actuator aligned with the deformable portion along the main axis and configured to actuate sequentially elongation and compression phases of the deformable portion,
wherein the deformable portion further comprises a wheel-platform which displays a first and a second face, the second face being configured to cooperate with the free end of the at least one spring element, in order to transform a back and forth movement of the at least one spring element into a rotational movement of the wheel-platform.

The invention therefore allows to create a tiny rotary micro-engine that can be millimetric and even sub-millimetric, transforming the mostly linear movement of a spring into a rotation.

The device according to the present invention may also include one or several of the following features, taken separately or in combination with each other:
the deformable portion may comprise a first spring element and a second spring element, the first spring element having a front end attached to the head portion and the second spring element having a rear end attached to the rear portion, each spring element displaying a free end,
the free end of each spring element may comprise at least one abutment member,
the first face of the wheel-platform may be configured to cooperate with the free end of the first spring element and the second face may be configured to cooperate with the free end of the second spring element, in order to transform a back and forth movement of both spring elements into a rotational movement of the wheel-platform,
the first and the second spring elements may be aligned along the main axis,
the actuator may be an electromagnetic actuator comprising an electromagnetic coil and a permanent magnet extending along the main axis,
the permanent magnet may translate back and forth at each spring element compression and elongation,
the first spring element may work in phase opposition with the second spring element,
each spring element may comprise at least three spring legs arranged helically relative to one another around the main axis,
each spring element may comprise a spring ring configured to join the at least three spring legs, said spring ring displaying at least three abutment members aimed at cooperating with the wheel-platform,
each abutment member may be an elastic strip,
each abutment member may be a pointy tooth,
the wheel-platform may be a notched wheel, each of the first and the second face displaying at least three notches, each notch being configured to cooperate with the abutment members of the corresponding spring element,
each spring element elongation may lead to a rotation of the wheel-platform, the rotation angle depending on the number of notches of the faces of the wheel-platform, the distance between two notches of the wheel-platform may be smaller than the course of one abutment element during a spring element elongation phase, each notch of the wheel-platform may display a first surface substantially perpendicular to a radius of the wheel-platform, said first surfaces being configured to cooperate, by abutment, with the abutment members of the first and second spring elements, a second surface extending between the first surface of a first notch and the first surface of a second notch, the second notch following the first notch along the wheel-platform circumference, said second surface being configured to cooperate, by sliding, with the abutment members of the first and second spring elements, each second surface of each notch may be inclined towards a center of the wheel-platform.

BRIEF DESCRIPTION OF THE DRAWINGS

Features and advantages of the invention will become apparent from the following description of several embodiments of a microrobot according to the invention, this description being given merely by way of example and with reference to the appended drawings in which.

DETAILED DESCRIPTION

In a first part of the current specification, the different elements of a micro-engine 10 according to the invention will be described. In a second part, the functioning of said micro-engine 10 will be explained.

A micro-engine 10 according to the invention aims at moving, along a main axis X (see FIG. 1), a micro-structure or any kind of micro-engineering device, through a viscous material such as the cerebrospinal fluid or the extracellular matrix of the brain of a subject. A viscous fluid is well knowingly defined as a fluidic material displaying a low Reynolds number.

In the present application, a micro-engine, or micro-motor, is considered to be an assembly of very small parts typically measured in microns that can move themselves. According to this definition, a micro-motor is, when linked to a micro-device, able to propel said micro-device, in a given direction autonomously when placed in water or a chemical solution, more often a viscous fluid material. A micro-engine might take any kind of shape and structure and there are many different micro-engines types operating under different mechanisms. The most important examples of micro-engines are biological engines such as, for example, the biological engines moving the flagella of self-propelled cells.

Regarding the current application, the micro-engine 10 comprises a rotation structure 12 which extends along the main axis X. The rotation structure 12 comprises a head portion 12A, a rear portion 12B and a deformable portion 14. The deformable portion 14 connects the head portion 12A and the rear portion 12B. The head portion 12A and the rear portion 12B are therefore connected along the main axis X. In the embodiment illustrated on FIGS. 2 and 8, each portion 12A, 12B is a flange platform displaying a central circular opening 15 (see FIG. 8) and external attachment strips.

Figure 1:
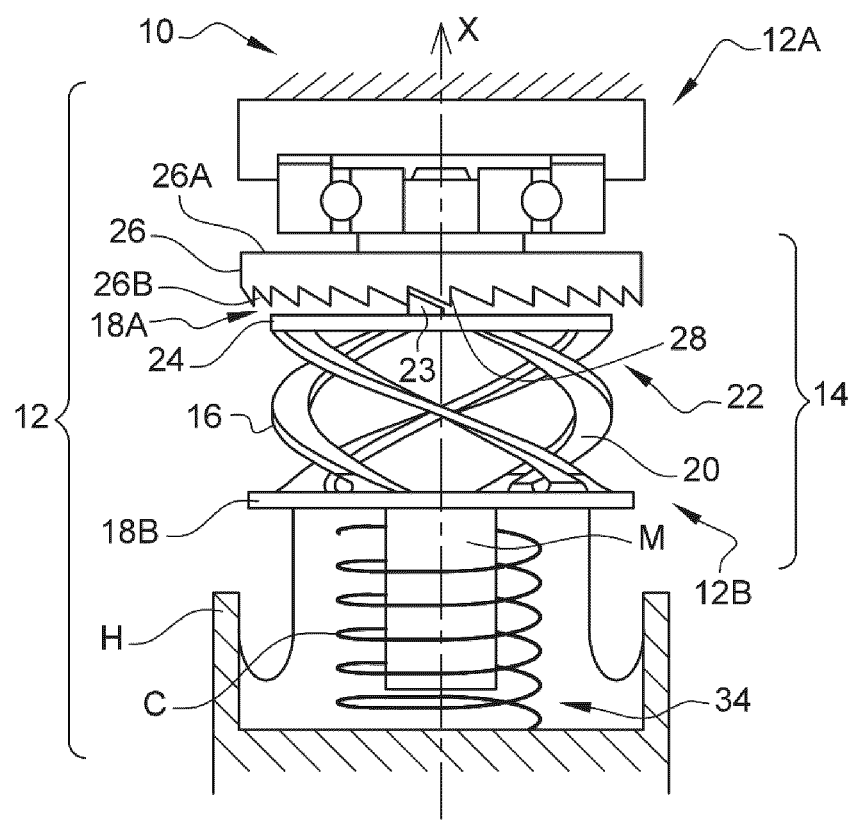
FIG. 1 is a schematic axial cut of a micro-engine according to a first embodiment of the invention.

On FIG. 1, the head portion 12A is a bearing, for example a ball bearing, aimed at maintaining the deformable portion 14 aligned with the main axis X while enabling the rotation of the rotation structure 12 and limiting friction. The rear portion 12B is a flange platform displaying an external attachment strip.

Figure 2:
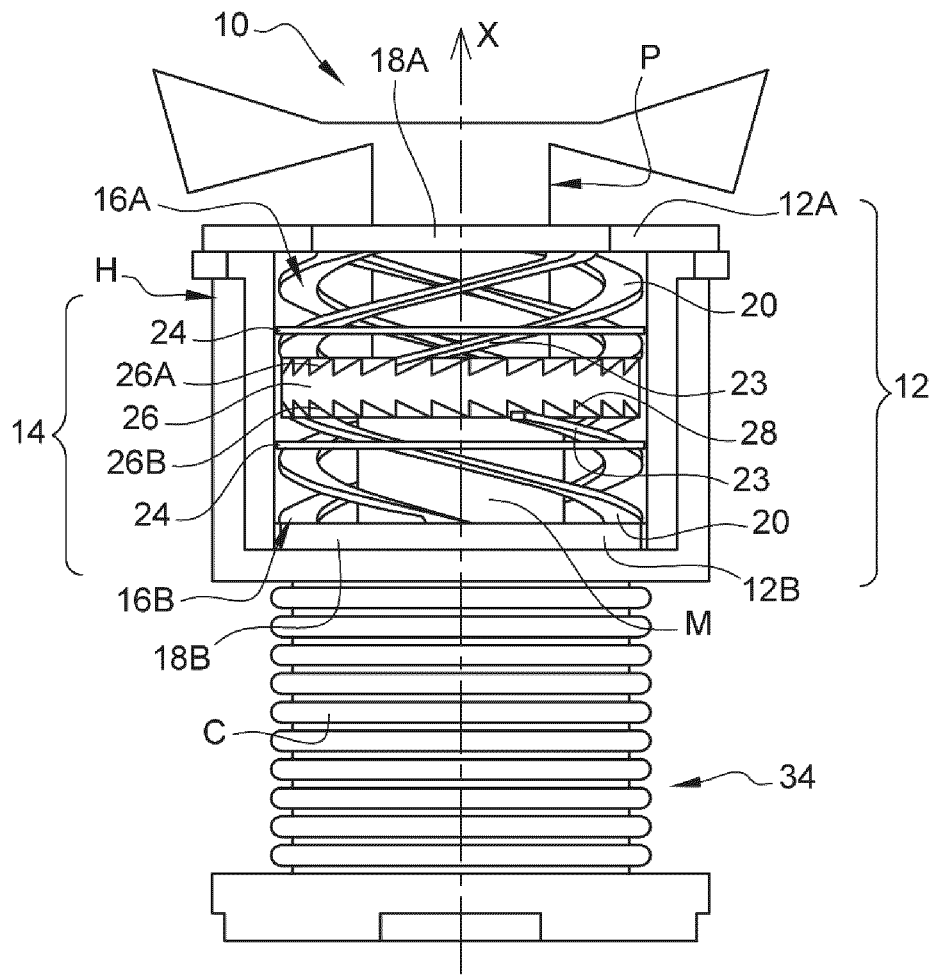
FIG. 2 is a schematic axial cut of a micro-engine according to a second embodiment of the invention comprising a propeller attached to the device according to the invention to illustrate an embodiment of an element that can be couple to the micro-engine according to the invention.

On FIGS. 1 and 2, it is to be seen that each attachment strip is attached to a rigid housing H enclosing the rotation structure 12. This housing H supports the rotation structure 12 and, in the embodiment of FIG. 2, enables its correct alignment along the main axis X. With regards to the embodiment of FIG. 2, said housing H extends along the main axis X and revolves around said main axis X. In some embodiments, this housing H also allows the rotation structure 12 to be protected from any fluidic intrusion. In this way, the rotary movement of the rotation structure 12 of the micro-engine 10 does not interfere with the linear movement (along the main axis X) of the viscous environment while the micro-structure is pushed forward by the micro-engine 10.

In a first embodiment, as depicted in FIG. 1, the deformable portion 14 comprises one spring element 16.

Figure 8:
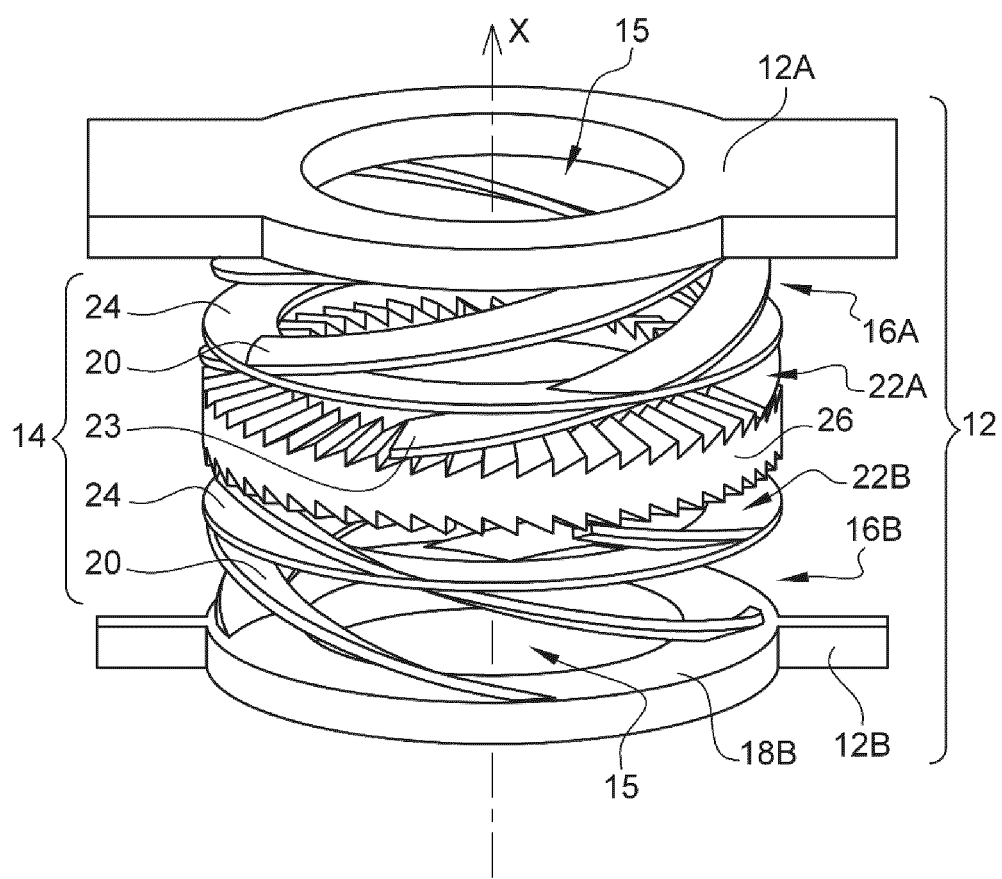
FIG. 8 is a perspective view of a rotation structure according to the second embodiment of the invention.

In a second embodiment, as depicted in FIGS. 2 and 8, the deformable portion 14 comprises two spring elements 16A and 16B.

Regarding the embodiment illustrated on FIG. 1, the deformable portion 14 comprises one spring element 16 extending along the main axis X. The deformable portion 14 is therefore deformable in elongation or compression along the main axis X. The spring element 16 is secured to the housing H in order to maintain it in place.

As illustrated on the embodiment of FIGS. 2 and 8, the deformable portion 14 comprises a first spring element 16A and a second spring element 16B each extending along the main axis X. More precisely, the first and the second spring elements 16A, 16B are aligned with each other along the main axis X, due to the housing H. The deformable portion 14 is therefore deformable in elongation or compression along the main axis X. The two spring elements 16A, 16B are secured to the housing H, the housing H assuring the two spring elements 16A, 16B to be secured at the right distance from each other.

Regarding FIG. 1, the spring element 16 has a rear end 18B attached to the rear portion 12B of the rotation structure 12. Regarding the embodiment of FIG. 2, the first spring element 16A has a front end 18A attached to the head portion 12A of the rotation structure 12. The second spring element 16B has a rear end 18B attached to the rear portion 12B of the rotation structure 12. Each spring elements 16A, 16B also comprises at least three spring legs 20. The spring element 16, 16A, 16B (16 and 16B not represented since identical to 16A) illustrated on FIG. 5 displays precisely three spring legs 20 arranged helically relative to one another around the main axis X.

Figure 3:
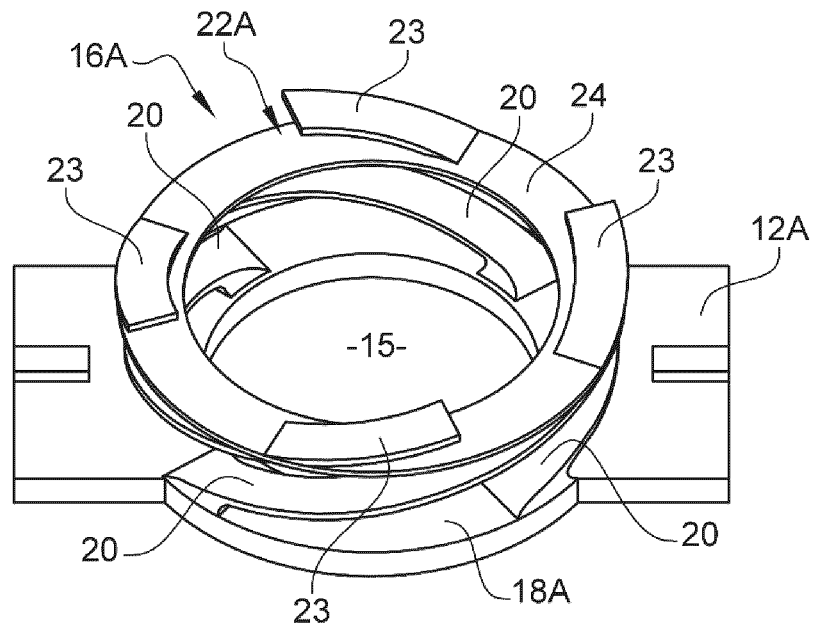
FIG. 3 is a perspective view of a spring element according to an embodiment of the current invention.

Regarding the embodiment of FIGS. 1 and 3, the spring element 16 has four spring legs 20 arranged helically relative to one another around the main axis X. As can be seen on FIG. 3, on the front end 18A of the spring element 16, the spring legs 20 are regularly arranged around the central circular opening 15 of the rear portion 12B. Regarding the embodiment shown on FIGS. 3 and 4, the spring elements 16A, 16B have four spring legs 20 arranged helically relative to one another around the main axis X. As can be seen on FIGS. 3 and 8, on the front end 18A of the first spring element 16A, the spring legs 20 are regularly arranged around the central circular opening 15 of the head portion 12A. On the rear end 18B of the second spring element 16B, the spring legs 20 are regularly arranged around the central circular opening 15 of the rear portion 12B. Preferably, each leg 20 of each spring 16, 16A, 16B displays a rectangular section with a width comprised between 60 and 300 µm, more preferably between 120 and 160 µm and a height comprised between 5 and 80 µm, more preferably between 20 and 40 µm. In an alternative embodiment, the legs 20 display a beveled section, said beveled section being inclined towards the inside of the deformable portion 14.

Preferably, the leg 20 displays a total length comprised between 300 and 600 µm, more preferably between 450 and 500 µm. In some embodiment, the legs 20 are made of a material comprising a UV-curable hybrid inorganic-organic polymer, such as, for example, OrmoClear®, displaying a Young's modulus comprises between 0.001 and 10 Gpa.

Each spring element 16, 16A, 16B further displays a free end 22, 22A, 22B (see FIGS. 1 and 8). Thus, each spring leg 20 of the spring element 16 (regarding FIG. 1) or of the second spring element 16B (regarding FIG. 2) extends from the rear portion 12B towards the head portion 12A, and, regarding the embodiment of FIG. 2, each spring leg 20 of the first spring element 16A extends from the head portion 12A towards the rear portion 12B. Therefore, as can be seen on FIGS. 2 and 8, the free end 22A of the first spring element 16A faces the free end 22B of the second spring element 16B.

Figure 4:
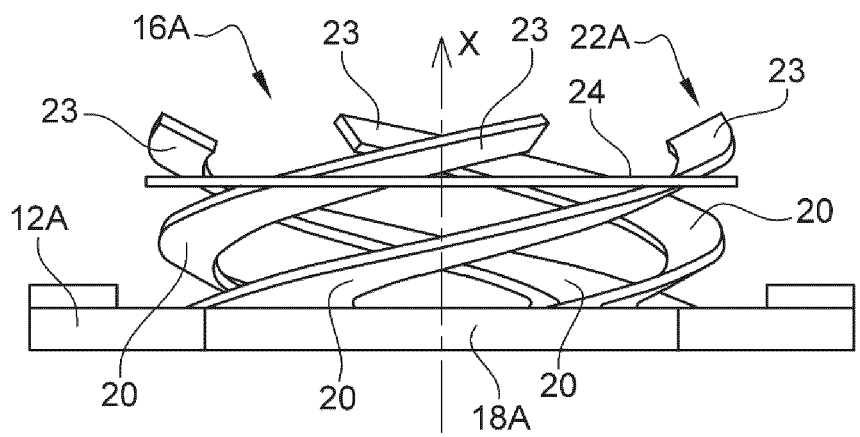
FIG. 4 is a side view of the spring element illustrated in FIG. 3.
Figure 6A:
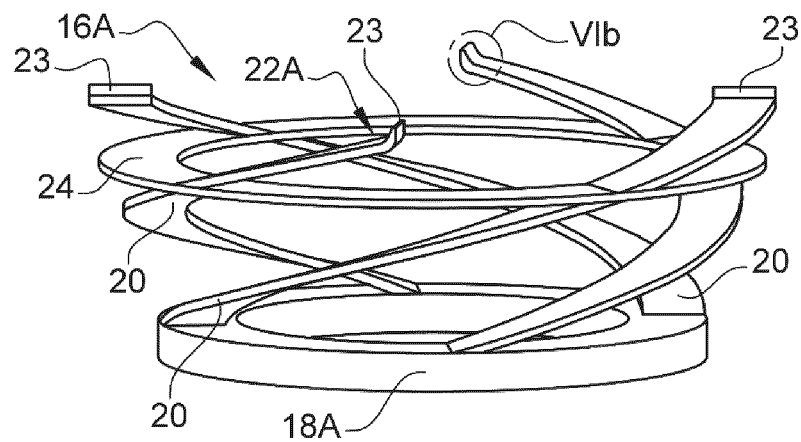
FIG. 6a is a side view of a spring element according to a third embodiment of the current invention.
Figure 6B:
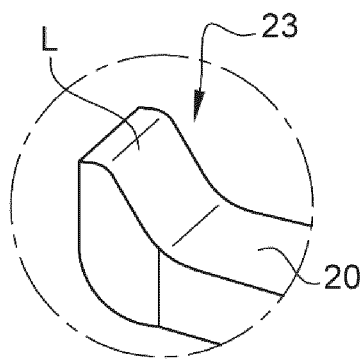
FIG. 6b is a detailed view of a spring element abutment of FIG. 6a, FIG. 7a is a perspective view of a wheel-platform according to the second embodiment of the invention.

The free end 22, 22A, 22B of each spring element 16, 16A, 16B comprises at least an abutment member 23. In the embodiments illustrated on FIGS. 3, 4, 6a and 8, each spring leg 20 of the spring elements 16, 16A, 16B displays, at its tip, an abutment member 23. In the embodiments of FIGS. 3, 4 and 8, each spring leg 20 ends in a straight edge and each of those edges forms an abutment member 23. In the embodiment illustrated on FIGS. 6a and 6b, each spring leg 20 of each spring element 16, 16A, 16B comprises, at its free end, a lug element L. In this embodiment, each lug element L forms an abutment member 23. The advantage of such a lug element L is to allow easier contact with the complementary notches 28 of the wheel-platform 26. The abutment contact obtained is therefore improved.

As can be seen on FIGS. 3 and 4, the spring element 16, 16A, 16B (elements 16 and 16B are not represented but are similar to element 16A which is represented) may comprise a spring ring 24 connecting its spring legs 20. The spring ring 24 joins the spring legs 20 of the spring element 16, 16A, 16B. This spring ring 24 reinforces the radial resistance of the spring element 16, 16A, 16B and avoids the spring legs 20 to depart from each other. This spring ring 24 also allows to better synchronize the movements of all the spring legs 20. In some embodiments, for example illustrated on FIG. 5, the spring ring 24 abuts against the free ends 22, 22A, 22B of the spring element 16, 16A, 16B. In that case, each spring leg 20 is connected, at its tip, to the spring ring 24 and the spring ring 24 becomes part of the free end 22, 22A, 22B of the spring element 16, 16A, 16B. In this kind of embodiment, the spring ring 24 displays at least three abutment members 23. In the embodiment illustrated on FIGS. 2, 3, 4 and 6a the spring ring 24 displays four abutment members 23. In the embodiment illustrated on FIG. 5, the spring ring 24 displays eight abutment members 23. In some embodiments, each abutment member 23 extending from the spring ring 24 is an elastic strip. In case the elastic strips are in same number that the spring legs 20 and are attached to the spring ring 24 in a way that shows continuity with the spring legs 20, this embodiment may look similar to the embodiments illustrated on FIGS. 3 and 4.

Figure 5:
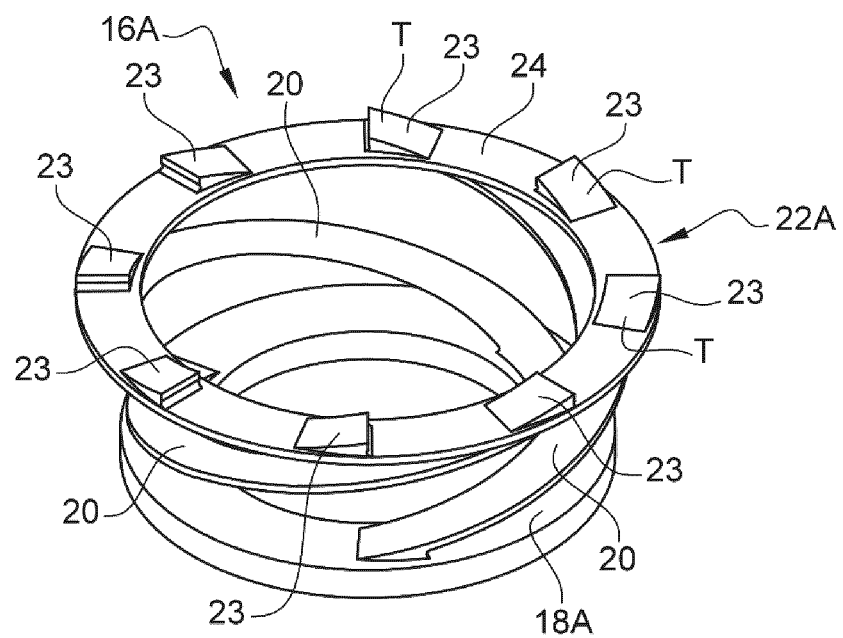
FIG. 5 is a perspective view of a spring element according to an embodiment of the current invention.

On the other hand, FIG. 5 illustrates an embodiment in which each abutment member 23 is a pointy tooth T.

In the embodiment illustrated on FIGS. 2 and 8, the spring elements 16A, 16B are substantially alike in shape and structure and each of them displays four spring legs 20.

As can be seen on FIGS. 1, 2 and 8, the deformable portion 14 further comprises a wheel-platform 26 which displays a central circular recess 25 (see FIG. 7a), a first face 26A and a second face 26B. When the rotation structure 12 is mounted and functional, the central circular recess 25 of the wheel-platform is aligned with the central circular openings 15 of the head and rear portions 12A, 12B.

Regarding FIG. 1, once the rotation structure 12 is mounted and functional, the first face 26A of the wheel-platform is maintained by the bearing of the head portion 12A, and the second face 26B of the wheel-platform 26 cooperates with the free end 22 of the spring element 16. Regarding FIG. 2, the free end 22A of the first spring element 16A cooperates with the first face 26A of the wheel-platform 26 and the second face 26B of the wheel-platform 26 cooperates with the free end 22B of the second spring element 16B.

Figure 7A:
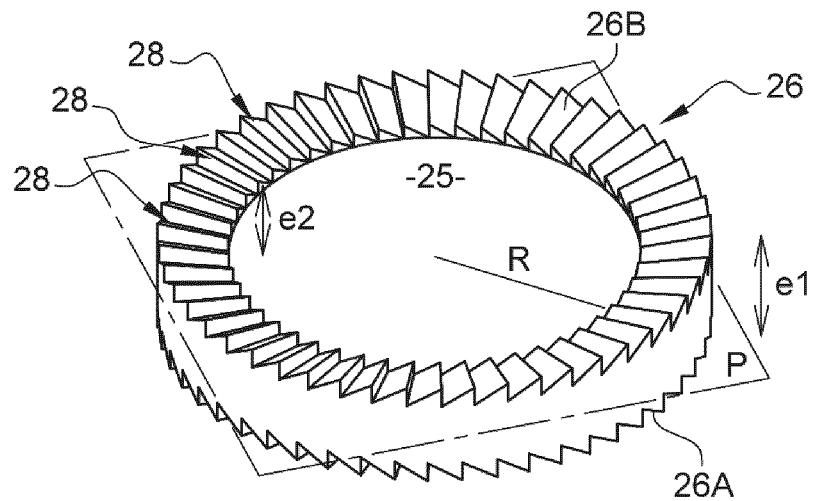
FIG. 7b is a side view of the wheel-platform of FIG. 7a, attached to a magnet
Figure 7B:
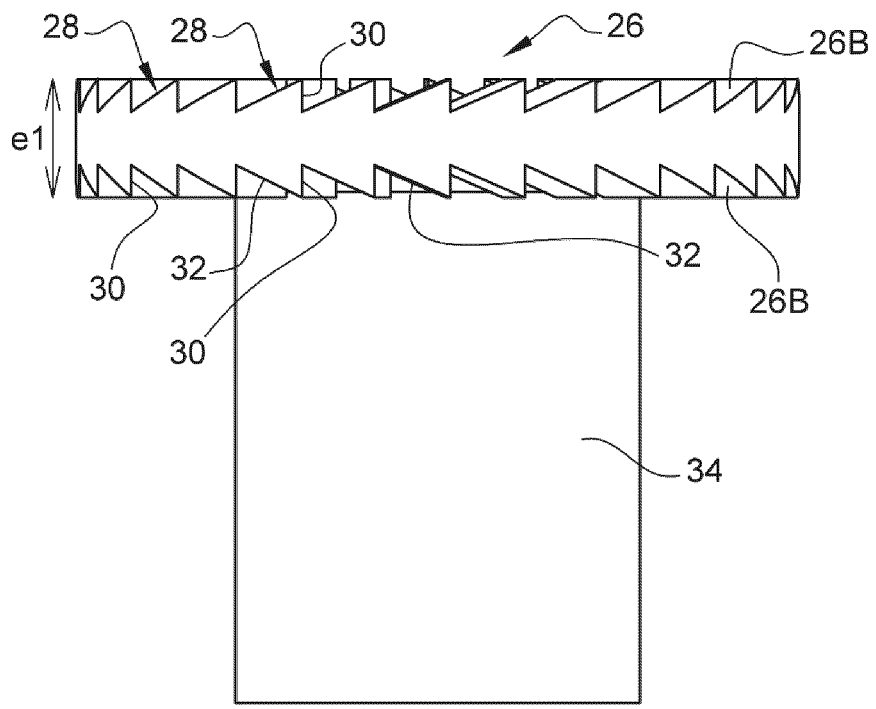

As can be seen on FIG. 7a, the wheel-platform 26 is a notched wheel and each of the first and the second faces 26A, 26B displays at least three notches 28. In the embodiment illustrated on FIG. 1, the wheel-platform 26 displays an asymmetrical shape: the first face 26A is a plain face and the second face 26B displays at least three notches 28. In the example illustrated on FIGS. 7a and 7b, the notched wheel displays more than three notches 28 on each face 26A, 26B, the higher the number the shorter the steps from one notch to another and vice-versa. Each face 26A, 26B comprises the same number of notches 28 and each notch 28 of the first face 26A corresponds to a notch 28 of the second face 26B in a way that confers the wheel platform 26 a transversal symmetry, according to a transversal plan P substantially perpendicular to the main axis X. Preferably, the wheel-platform 26 displays a radius R comprised between 100 and 1500 µm, more preferably between 500 and 1300 µm. Each notch 28 mays have a height comprised between 30 and 50 µm. Further, each notch 28 of the wheel-platform 26 displays a first and a second surfaces 30, 32 (see FIG. 7b). The first surface 30 is substantially perpendicular to the wheel-platform radius R and to the transverse plan P of the wheel-platform 26 as shown in FIG. 7a, said first surface 30 also extending along the main axis X. The plan P comprises the surface of the recess 25, this plan is defined as a plan perpendicular to the axis of the wheel-platform 26. The second surface 32 extends between the first surface 30 of a first notch 28 and the first surface 30 of a second notch 28, the second notch 28 following the first notch 28 along the wheel-platform 26 circumference. Further, each second surface 32 of each notch 28 is inclined towards the center of the wheel-platform 26. This inclination is between 1° and 35°, preferably about 10° C. with regards to the surface of the recess 25. The terminology "about" refers to the measurement error margin. This gives each face 26A, 26B of the wheel-platform 26 a general shape of an inverted cone basis converging towards the wheel center. This way, the thickness $e_1$ of the platform-wheel 26 at its outer circumference is greater than its thickness $e_2$ at its inner circumference, as can be seen on FIG. 7a. This allows a better coupling between the wheel-platform 26 and the free ends 22A, 22B, the risk of wheel disengagement is significantly lowered.

Each notch 28 is configured to cooperate with the abutment members 23 of the free ends 22A, 22B of the corresponding spring elements 16A, 16B.

Figure 9A:
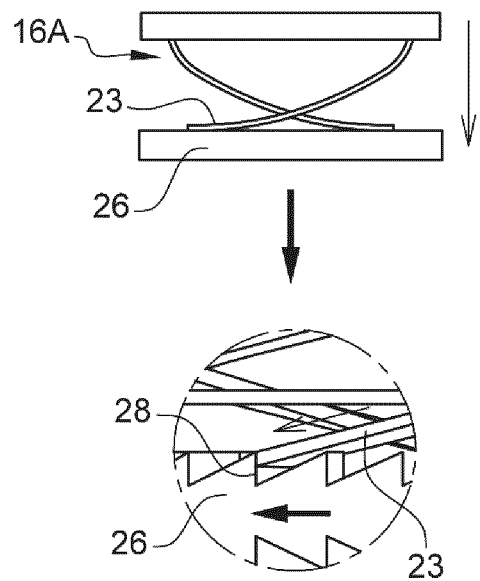
FIGS. 9a and 9b are schematic illustrations of a spring leg movement with regards of the wheel-platform during respectively a compression phase of the spring element and an elongation phase of the spring element according to the invention.
Figure 9B:
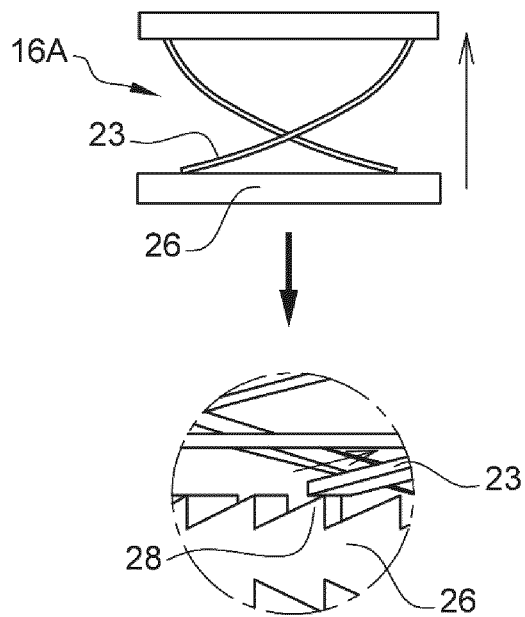

Therefore, regarding FIG. 1, once the rotation structure 12 is mounted and functional, each abutment member 23 of the spring element 16 cooperates with the notches 28 of the second face 26B of the wheel-platform 26, as illustrated in detail on FIGS. 9a and 9b. Regarding FIG. 2, each abutment member 23 of the first spring element 16A cooperates with the notches 28 of the first face 26A of the wheel-platform 26, and each abutment member 23 of the second spring element 16B cooperates with the second face 26B of the wheel-platform 26, as illustrated in detail on FIGS. 9a and 9b.

More precisely, each first surface 30 is configured to cooperate, by abutment, with the abutment members 23 of each spring elements 16, 16A, 16B, and each second surface 32 is configured to cooperate, by sliding, with the abutment members 23 of each spring element 16, 16A, 16B. It is therefore important to give the abutment members 23 specific shapes enabling improvement of the abutting against the first surface 30 as well as the sliding over the second surface 32 (see FIGS. 9a and 9b).

As can be seen on FIGS. 1 and 2, the rotation structure 12 further comprises an actuator 34 configured to actuate the spring elements 16, 16A, 16B. The actuator 34 therefore sequentially induces elongation and compression phases of the deformable portion 14. As can be seen on FIGS. 1 and 2, the actuator 34 is aligned, along the main axis X with the rotation structure 12.

In some embodiments (see FIGS. 1 and 2), the actuator 34 is an electromagnetic actuator comprising an electromagnetic coil C and a permanent magnet M.

In other embodiments (not shown), the actuator 34 may be a fluidic pump. In another embodiment, the spring elements 16, 16A, 16B may comprise a micro light sensitive array and be directly activated by a light source, for example, a laser. In a further embodiment, the spring legs 20 may comprise some electroactive polymers and therefore react to an electric field and change size or shape when stimulated.

In the embodiment of FIG. 1, the permanent magnet M extends along the main axis X, from the rear portion 12B in the opposite direction of the spring element 16. The permanent magnet M is inside the casing H. The coil C extends around the permanent magnet M. In this embodiment, the permanent magnet M is secured to the rear end 18B of the spring element 16 and, depending on the current applied to the coil C, the magnet M moves either back or forth and the spring element 16 moves along with it. The back and forth translation of the permanent magnet M induces the spring element 16 to elongate or compress, depending on the phase. Phases will be defined further below.

With the actuator 34 aligned with the spring element 16 along the main axis X and more particularly in case of a an electromagnetic actuator comprising an electromagnetic coil C and a permanent magnet M, with only one coil C centered around the permanent magnet M, the micro-engine 10 diameter can be reduced to the sub-millimetric size and therefore be integrated in a micro-engineering process.

Once the spring element 16 is activated and put into motion, the cooperation between the surfaces 30, 32 of the notches 28 with the abutment members 23 of the spring element 16 enables to transform the back and forth movement of the spring element 16 into a rotational movement of the wheel-platform 26.

In the embodiment of FIG. 2, the permanent magnet M extends along the main axis X between the rear portion 12B and the central recess 25, through the central circular openings 15 of the rear portion 12B. The permanent magnet M translates back and forth towards each spring element 16A, 16B during their respective compression and elongation phases. More precisely, the permanent magnet M is secured to the wheel-platform 26 and the wheel-platform 26 moves along with the permanent magnet M. Depending on the current applied to the electromagnetic coil C, the magnet M moves either back or forth. The back and forth translation of the wheel-platform 26 induces the spring elements 16A, 16B to elongate or compress, depending on the phase. Phases will be defined further below.

With the actuator 34 aligned with the spring elements 16A, 16B along the main axis X, the micro-engine 10 diameter can, similarly as for the embodiment of FIG. 1, be reduced to the sub-millimetric size and therefore be integrated in a micro-engineering process. This is particularly the case of an electromagnetic actuator 34 comprising an electromagnetic coil C and a permanent magnet M, with only one coil C centered around the main axis X.

Once the spring elements 16A, 16B are activated and put into motion, the cooperation between the surfaces 30, 32 of the notches 28 with the abutment members 23 of the spring elements 16A, 16B enables to transform the back and forth movement of both spring elements 16A, 16B into a rotational movement of the wheel-platform 26. The permanent magnet M rotates with the wheel-platform 26. This rotational movement of the wheel-platform 26 further enables to rotate the micro-structure connected to the micro-engine 10.

For example, on FIG. 2, a propeller P is attached to the wheel-platform 26. When the wheel-platform 26 is put into motion, the propeller P follows the rotation and is put into motion too.

More precisely, in a case where the actuator 34 is an electromagnetic actuator (example of FIGS. 1 and 2), when the micro-engine 10 is turned on, the permanent magnet M starts translating up and down along the main axis X. This translation movement is transmitted to the spring elements 16, 16A, 16B and more particularly to the spring legs 20. The tip of each spring legs 20 therefore translates up and down too. However, due to their helicoidal shape, said spring legs 20 also undergo a tiny rotation around the main axis X. This rotation is transmitted, by means of the abutment member 23 to the notches 28 of the platform-wheel 26 and therefore transmitted to the platform-wheel 26 in its whole. Additionally, the embodiment of FIG. 2 enables a continuous rotation of the wheel-platform 26, the first spring element 16A works in phase opposition with the second spring element 16B.

In classical mechanics, a spring element can theoretically be assimilated to a harmonic oscillator. Regarding the current invention, it is obvious that many other elements interfere in the definition of the movement equation of the spring elements 16A, 16B. However, in order to define a phase, this simple theoretical model is sufficient. A harmonic oscillator is a system that, when displaced from its equilibrium position, experiences a restoring force $\vec{F}$ proportional to the displacement $\vec{x}$:

$$\vec{F} = -k\vec{x} \text{ where } k \text{ is a positive constant.}$$

In the case of FIG. 1, there is only one spring element 16 displaying a constant k. In the case of FIG. 2, the spring elements 16A, 16B are positioned in series along the main axis X. The constant k is therefore the equivalent stiffness of both the spring elements 16A, 16B and k is the sum of the constants $k_A$ and $k_B$ of both spring elements 16A, 16B: $k = k_A + k_B$. The displacement of the spring elements 16A, 16B are along the main axis X and $\vec{x}$ can therefore be positive or negative (over or below 0), regarding the direction of the movement of the each spring element 16, 16A, 16B with regards to the main axis X: either the free end 22A, 22B of the spring element 16, 16A, 16B is moving towards the wheel-platform 26 (compression phase in case of the embodiment of FIG. 1 and elongation phase in case of the embodiment of FIG. 2) or the free end 22A, 22B is moving away from the wheel platform 26 (elongation phase in case of the embodiment of FIG. 1 and compression phase in case of the embodiment of FIG. 2). One phase is defined, in the current application, as the whole movement of the spring element 16, 16A, 16B before $\vec{x}$ changes sign. Each spring element 16, 16A, 16B moves along the main axis X but, regarding FIG. 2, in opposite directions as their free ends 22A, 22B face each other. Regarding FIG. 1, the spring element 16 is therefore considered to be in elongation phase when its displacement is negative (below 0) and in compression phase when its displacement is positive (over 0). Regarding FIG. 2, the first spring element 16A is therefore considered to be in elongation phase when its displacement $\vec{x}$ is positive (over 0) and in compression phase when its displacement $\vec{x}$ is negative (below 0). The second spring element 16B is, on the opposite, considered to be in elongation phase when its displacement $\vec{x}$ is negative and in compression phase when its displacement $\vec{x}$ is positive. This way, the first spring element 16A enters a compression phase when the second spring element 16B enters an elongation phase.

Obviously, regardless of the embodiment, the spring elements 16, 16A, 16B are in a pre-constrained state during assembly.

As each spring elements 16, 16A, 16B elongation leads to a rotation of the wheel-platform 26, the wheel-platform 26 is therefore rotated at each compression/elongation phase of the deformable part 14 as one of the spring elements 16, 16A, 16B is necessarily in an elongation phase. The rotation angle of the wheel-platform 26 during each compression/elongation phase of the deformable part 14 depends on the number of notches 28 of the faces 26A, 26B of the wheel-platform 26. In embodiments where the distance between two notches 28 is smaller than the course of one abutment element 23 during the spring elements 16, 16A, 16B compression/elongation, the wheel-platform 26 is continuously rotated. The more notches 28 there are on the wheel-platform 26, the smoother the rotation of said wheel-platform 26.

Even if continuous, the rotation of the wheel-platform 26 is slow since each compression/elongation of the spring elements 16, 16A, 16B allows for one single notch 28 advancement. However, the torque of the rotation is strong because of those small increments. It acts like a gearbox. The more notches 28 there are on the wheel-platform 16, the more torque the rotation gets. Passive gear boxing can be achieved by playing on the number of notches 28 during design and fabrication.

The invention claimed is:

1. A micro-engine configured to move a micro-structure, the micro-engine comprising a rotation structure, said rotation structure comprising a head portion, a rear portion and a deformable portion connecting the head portion and the rear portion,
    wherein the deformable portion is deformable in elongation or compression along a main axis extending from the head portion to the rear portion,
    wherein the deformable portion comprises at least one spring element, the at least one spring element having a rear end attached to the rear portion, the at least one spring element has a free end,
    wherein the free end of the at least one spring element comprises at least one abutment member,
    wherein the rotation structure further comprises an actuator aligned with the deformable portion along the main axis and configured to actuate sequentially elongation and compression phases of the deformable portion,
    wherein the deformable portion further comprises a wheel-platform which has a first and a second face, the second face being configured to cooperate with the free end of the at least one spring element, in order to transform a back-and-forth movement of the at least one spring element into a rotational movement of the wheel-platform.

2. The micro-engine according to claim 1, wherein the deformable portion comprises a first spring element and a second spring element, the first spring element having a front end attached to the head portion and the second spring element having a rear end attached to the rear portion, each spring element has a free end,
    wherein the free end of each spring element comprises at least one abutment member, wherein the first face of the wheel-platform is configured to cooperate with the free end of the first spring element and the second face is configured to cooperate with the free end of the second spring element, in order to transform a back-and-forth movement of both spring elements into a rotational movement of the wheel-platform.

3. The micro-engine according to claim 2, wherein the first and the second spring elements are aligned along the main axis.

4. The micro-engine according to claim 1, wherein the actuator is an electromagnetic actuator comprising an electromagnetic coil and a permanent magnet extending along the main axis.

5. The micro-engine according to claim 4, wherein the permanent magnet translates back and forth when the at least one spring element compresses and elongates.

6. The micro-engine according to claim 2, wherein the first spring element works in phase opposition with the second spring element.

7. The micro-engine according to claim 1, wherein the at least one spring element comprises at least three spring legs arranged helically relative to one another around the main axis.

8. The micro-engine according to claim 1, wherein the at least one spring element comprises a spring ring configured to join at least three spring legs, said spring ring has at least three abutment members configured to cooperate with the wheel-platform.

9. The micro-engine according to claim 1, wherein the at least one abutment member is an elastic strip.

10. The micro-engine according to claim 1, wherein the at least one abutment member is a pointy tooth.

11. The micro-engine according to claim 1, wherein the wheel-platform is a notched wheel, each of the first and the second face having at least three notches, each notch being configured to cooperate with the at least one abutment member of the at least one spring element.

12. The micro-engine according to claim 11, wherein spring element elongation leads to a rotation of the wheel-platform, wherein the rotation angle depends on a number of notches on the faces of the wheel-platform.

13. The micro-engine according to claim 11, wherein a distance between two notches of the wheel-platform is smaller than a course of one of the at least one abutment element during a spring element elongation phase.

14. The micro-engine according to claim 11, wherein the at least one spring element includes a first spring element and a second spring element, and wherein each notch of the wheel-platform has:
   a first surface substantially perpendicular to a radius of the wheel-platform, said first surface being configured to cooperate, by abutment, with each of the at least one abutment members of the first spring element and the second spring element,
   a second surface extending between the first surface of a first notch and the first surface of a second notch, the second notch following the first notch along the wheel-platform circumference, said second surface being configured to cooperate, by sliding, with each of the at least one abutment members of the first and second spring elements.

15. The micro-engine according to claim 14, wherein each second surface of each notch is inclined towards a center of the wheel-platform.

* * * * *